(12) United States Patent
Budiman et al.

(10) Patent No.: US 9,579,456 B2
(45) Date of Patent: Feb. 28, 2017

(54) METHODS FOR REDUCING FALSE HYPOGLYCEMIA ALARM OCCURRENCE

(75) Inventors: Erwin S. Budiman, Fremont, CA (US); Gary A. Hayter, Oakland, CA (US); Marc B. Taub, Mountain View, CA (US); Roman Hovorka, Cambridge (GB); Malgorzata Wilinska, Cambridge (GB); David Dunger, Cambridge (GB)

(73) Assignees: ABBOTT DIABETES CARE INC., Alameda, CA (US); CAMBRIDGE ENTERPRISE LIMITED, Cambridge (GB)

( * ) Notice: Subject to any disclaimer, the term of this patent is extended or adjusted under 35 U.S.C. 154(b) by 997 days.

(21) Appl. No.: 12/784,981

(22) Filed: May 21, 2010

(65) Prior Publication Data

US 2010/0317952 A1    Dec. 16, 2010

Related U.S. Application Data

(60) Provisional application No. 61/180,700, filed on May 22, 2009, provisional application No. 61/180,627, filed on May 22, 2009, provisional application No. 61/180,649, filed on May 22, 2009, provisional application No. 61/180,774, filed on May 22, 2009, provisional application No. 61/180,767, filed on May 22, 2009.

(51) Int. Cl.
| | |
|---|---|
| *A61B 5/00* | (2006.01) |
| *A61M 5/172* | (2006.01) |
| *A61B 5/145* | (2006.01) |
| *A61M 5/142* | (2006.01) |
| *G06F 19/00* | (2011.01) |

(52) U.S. Cl.
CPC ....... *A61M 5/1723* (2013.01); *A61B 5/14532* (2013.01); *A61B 5/4839* (2013.01); *A61B 5/7275* (2013.01); *A61M 2005/14296* (2013.01); *A61M 2205/18* (2013.01); *A61M 2205/3569* (2013.01); *A61M 2205/52* (2013.01); *A61M 2230/201* (2013.01); *G06F 19/345* (2013.01); *G06F 19/3437* (2013.01); *G06F 19/3468* (2013.01); *G06F 19/3487* (2013.01)

(58) Field of Classification Search
CPC .................................................... A61B 5/14532
USPC ........................................ 600/345, 347, 365
See application file for complete search history.

(56) References Cited

U.S. PATENT DOCUMENTS

| | | | |
|---|---|---|---|
| 5,822,715 A | 10/1998 | Worthington et al. | |
| 7,583,990 B2 * | 9/2009 | Goode et al. | 600/347 |
| 2003/0100821 A1 * | 5/2003 | Heller et al. | 600/347 |
| 2003/0125612 A1 * | 7/2003 | Fox et al. | 600/347 |

(Continued)

FOREIGN PATENT DOCUMENTS

| | | |
|---|---|---|
| JP | 2005087640 A | 4/2005 |
| JP | 2007000188 A | 1/2007 |
| WO | 2005065538 A2 | 7/2005 |

*Primary Examiner* — Christian Jang
(74) *Attorney, Agent, or Firm* — One LLP

(57) ABSTRACT

A system and method for reducing the number of hypoglycemic alarms presented to a user is presented. The system and methods include use of model based state estimation and variable-delayed threshold values to balance the risk of not presenting an alarm caused by an actual hypoglycemic state with the presentation of alarms caused by artifacts in the signals produced by a continuous glucose monitor.

19 Claims, 6 Drawing Sheets

(56) References Cited

U.S. PATENT DOCUMENTS

| | | |
|---|---|---|
| 2007/0078314 A1 | 4/2007 | Grounsell et al. |
| 2007/0173761 A1 | 7/2007 | Kanderian, Jr. et al. |
| 2008/0071157 A1* | 3/2008 | McGarraugh et al. ....... 600/347 |
| 2008/0086042 A1* | 4/2008 | Brister et al. ................. 600/347 |
| 2008/0228056 A1* | 9/2008 | Blomquist et al. ........... 600/365 |

* cited by examiner

METHODS FOR REDUCING FALSE HYPOGLYCEMIA ALARM OCCURRENCE

CROSS-REFERENCES TO RELATED APPLICATIONS

This application claims the benefit of U.S. Provisional Application No. 61/180,700, filed May 22, 2009, which is incorporated herein by reference in its entirety.

This application also claims the benefit of and is related to U.S. Provisional Application No. 61/180,627, filed May 22, 2009, U.S. Provisional Application No. 61/180,649, filed May 22, 2009, U.S. Provisional Application No. 61/180,774, filed May 22, 2009, and U.S. Provisional Application No. 61/180,767, filed May 22, 2009.

BACKGROUND

Diabetes is a metabolic disorder that afflicts tens of millions of people throughout the world. Diabetes results from the inability of the body to properly utilize and metabolize carbohydrates, particularly glucose. Normally, the finely tuned balance between glucose in the blood and glucose in bodily tissue cells is maintained by insulin, a hormone produced by the pancreas which controls, among other things, the transfer of glucose from blood into body tissue cells. Upsetting this balance causes many complications and pathologies including heart disease, coronary and peripheral artery sclerosis, peripheral neuropathies, retinal damage, cataracts, hypertension, coma, and death from hypoglycemic shock.

In persons with insulin-dependent diabetes, the symptoms of the disease can be controlled by administering additional insulin (or other agents that have similar effects) by injection or by external or implantable insulin pumps. The "correct" insulin dosage is a function of the level of glucose in the blood. Ideally, insulin administration should be continuously readjusted in response to changes in glucose level.

Presently, systems are available for continuously monitoring a person's glucose levels by implanting a glucose sensitive probe into the person. Such probes measure various properties of blood or other tissues, including optical absorption, electrochemical potential and enzymatic products. The output of such sensors can be communicated to a hand held device or controller that is used to calculate an appropriate dosage of insulin to be delivered to the user of the continuous glucose monitor (CGM) in view of several factors, such as the user's present glucose level, insulin usage rate, carbohydrates consumed or to be consumed and exercise, among others. These calculations can then be used to control a pump that delivers the insulin, either at a controlled "basal" rate, or as a "bolus" into the user. When provided as an integrated system, the continuous glucose monitor, controller and pump work together to provide continuous glucose monitoring and insulin pump control.

Such systems can be closed loop systems, where the amount of insulin being delivered is completely controlled by the controller and pump in conjunction with glucose level data received from the CGM device. Alternatively, such systems may be open loop systems, where the user evaluates the glucose level information from a glucose monitoring device and then instructs the pump accordingly, or the system may be a semi-closed loop system that combines various aspects of a closed loop and open loop system.

Typically, present systems may be considered to be open or semi-closed loop in that they require intervention by a user to calculate and control the amount of insulin to be delivered. However, there may be periods when the user is not able to adjust insulin delivery. For example, when the user is sleeping, he or she cannot intervene in the delivery of insulin, yet control of a patient's glucose level is still necessary. A system capable of integrating and automating the functions of glucose monitoring and controlled insulin delivery into a closed loop system would be useful in assisting users in maintaining their glucose levels, especially during periods of the day when they are unable or unwilling to the required calculations to adjust insulin deliver to control their glucose level.

What has been needed, and heretofore unavailable, is an integrated, automated system combining continuous glucose monitoring and controlled insulin delivery. Such a system would include various features to insure the accuracy of the glucose monitor and to protect the user from either under- or over-dosage of insulin. The system would include various functions for improving the usability, control, and safety of the system, including a variety of alarms which could be set by a user or a technician to avoid false alarms while ensuring adequate sensitivity to protect the user. The present invention satisfies these and other needs.

SUMMARY OF THE INVENTION

Briefly, and in general terms, the invention is directed to new and improved systems and methods for management of glucose level management, including systems and methods for improving the usability and safety of systems including continuous glucose monitors and a drug delivery pumps.

In one aspect, the invention includes programming a processor to be responsive to an input to determine whether an alarm should be presented to a user indicating that a hypoglycemic condition exists, and if so, determine when to present the alarm to the user.

In another aspect, the state machine comprises a CGM based subsystem that is described in terms of a state machine governing the behavior of the assertion of a CGM based hypoglycemia detection and alarm mechanism and a glucose level based subsystem that is described in terms of a state machine that governs how and when confirmatory glucose level measurements should be taken, how and when rescue carbohydrates should be administered, and when to de-assert the CGM based hypoglycemia detector.

In still another aspect, the system also uses historical information, such as, for example, previous glucose measurements and insulin delivery history to set a variable delay dependent on a future prediction of glucose level before sounding an alarm. In an alternative embodiment, a look up table may be used to modify the duration of the timer.

In yet another aspect, the present invention includes a system for monitoring the glucose level of a user, comprising: a continuous glucose monitor; a processor configured to receive signals from the continuous glucose monitor and also adapted to analyze those signals in accordance with software commands, the software commands including commands to program at least a portion of the processor to operate as a state machine, the state machine having a first state when the signals from the continuous glucose monitor indicate a not hypoglycemic state and a second state when the signals indicate that a glucose value is below a selected threshold value.

In an alternative aspect, the second state includes starting a timer to delay presentation of an alarm to the user, the delay determined by the glucose value; and in still another alternative aspect, the second state includes presenting an alarm to the user and requesting a confirmation measurement of glucose level when the glucose value is below a second selected threshold value that is lower than the first threshold value. In still a further aspect, the second state includes recommending administration of rescue carbohydrates if the confirmation measurement glucose value is below a selected threshold. In yet another aspect, the present invention, an alarm is presented to the user at the expiration of the delay if the signal from the continuous glucose monitor indicates that the glucose value is still below the threshold value.

In still another aspect, the present invention includes a method for determining when to present a hypoglycemic alarm to a user of a continuous glucose monitor, comprising: providing a controller programmed to operate as a state machine; providing signals from a continuous glucose monitor as input to the state machine; wherein the state machine operates in accordance with the programming and the input to determine if an alarm is to be presented to the user indicating that an actual hypoglycemic condition exists.

In yet another aspect, the present invention includes a system for monitoring the glucose level of a user, comprising: a continuous glucose monitor configured to transmit signals representative of a glucose value; a processor configured to receive signals from the continuous glucose monitor and also adapted to analyze those signals in accordance with software commands, the software commands including commands to program at least a portion of the processor to operate as an alarm specificity optimizing system, the alarm specificity system having a first subsystem where temporal behavior of the signals from the continuous glucose monitor is used to maximize the specificity of a hypoglycemic event detection and assert a hypoglycemic alarm, and a second subsystem where one or more glucose level measurements is used to ensure whether or not the hypoglycemic event has been resolved.

In an alternative aspect, optimization of the alarm specificity includes having the first subsystem starting one or more timers to delay presentation of an alarm to the user, wherein the delay for each timer is a function of the level of hypoglycemia indicated by signals received from the continuous glucose monitor. In another alternative aspect, the second subsystem includes requesting a confirmation measurement of glucose level when the first subsystem presents an alarm or when a value of a previous glucose level measurement is below a selected threshold value. In still another alternative aspect, the second subsystem includes recommending administration of rescue carbohydrates if the confirmation measurement glucose value is below a selected threshold.

In still another alternative aspect, the second subsystem utilizes temporal glucose information and other relevant information to aid in minimizing false alarms by determining the appropriate amount of delay since the latest glucose level measurement that confirms a non-hypoglycemic event before the first subsystem can start detecting hypoglycemic events again. In yet another alternative aspect, an alarm is presented to the user at the expiration of the delay if the signal from the continuous glucose monitor indicates that the glucose value is still below the threshold value; and in a further alternative aspect, the delay can be zero if the glucose measurement is below a low glucose threshold value.

In still another aspect, the present invention includes a method for determining when to present a hypoglycemic alarm to a user of a continuous glucose monitor, comprising: providing at least one timer to track the amount of time since one or more low glucose value thresholds have been passed; providing signals from a continuous glucose monitor as an input to a processor controlling the operation of the at least one timer; presenting a hypoglycemic alarm when the at least one timer has elapsed; requesting a glucose level measurement to verify a hypoglycemic event; utilizing glucose level measurements to determine whether the at least one timer should reset and start over; utilizing continuous glucose measurements, knowledge of a meal, knowledge of insulin delivery, and other physiologically relevant information in order to determine the amount of time before the at least one timer can be reset and start detecting hypoglycemic events again since the last time a glucose level measurement confirms that the patient is no longer in a hypoglycemic state; utilizing glucose level measurements to suggest corrective action such as taking rescue carbohydrates when the latest glucose level measurement confirms that the patient is in a hypoglycemic state; and wherein the processor operates in accordance with suitable programming and the input to determine if an alarm is to be presented to the user indicating that an actual hypoglycemic condition exists.

In another aspect, the present invention includes a method for determining when to present a hypoglycemic alarm to a user of a continuous glucose monitor, comprising: providing a plurality timers to track the amount of time since one or more low glucose value thresholds have been passed; providing signals from a continuous glucose monitor as a primary input to the system; presenting a hypoglycemic alarm when any one of the plurality of timers has elapsed past its corresponding limit; requesting a glucose level measurement to verify the hypoglycemic event; utilizing glucose level measurements to confirm the predicted hypoglycemic event; utilizing continuous glucose measurements, knowledge of a meal, knowledge of insulin delivery, and other physiologically relevant information in order to determine the amount of time before the plurality of timers can reset and start detecting hypoglycemic events again since the last time a glucose level measurement confirms that the patient is no longer in a hypoglycemic state; wherein the system operates in accordance with suitable programming and the input to determine if an alarm is to be presented to the user indicating that an actual hypoglycemic condition exists.

In yet another aspect, the present invention includes a system for monitoring the glucose level of a user, comprising: a continuous glucose monitor; a processor configured to receive signals from the continuous glucose monitor and also adapted to analyze those signals in accordance with software commands, the software commands including commands to program at least a portion of the processor to operate as a state machine, the state machine having a first state when the signals from the continuous glucose monitor are used to predict threshold detection with minimal annunciation of a false alarm with respect to signal artifacts and a second state when the signals confirm the event prediction. In an alternative aspect, the second state includes minimizing the false alarm with respect to signal artifacts by starting a timer to delay presentation of an alarm to the user, the delay determined by the glucose value.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

For the purposes of promoting an understanding of the principles of the invention, reference will now be made to a number of illustrative embodiments shown in the attached drawings and specific language will be used to describe the same. It will be understood that throughout this document, the terms "user" and "patient" are used interchangeably.

Figure 1:
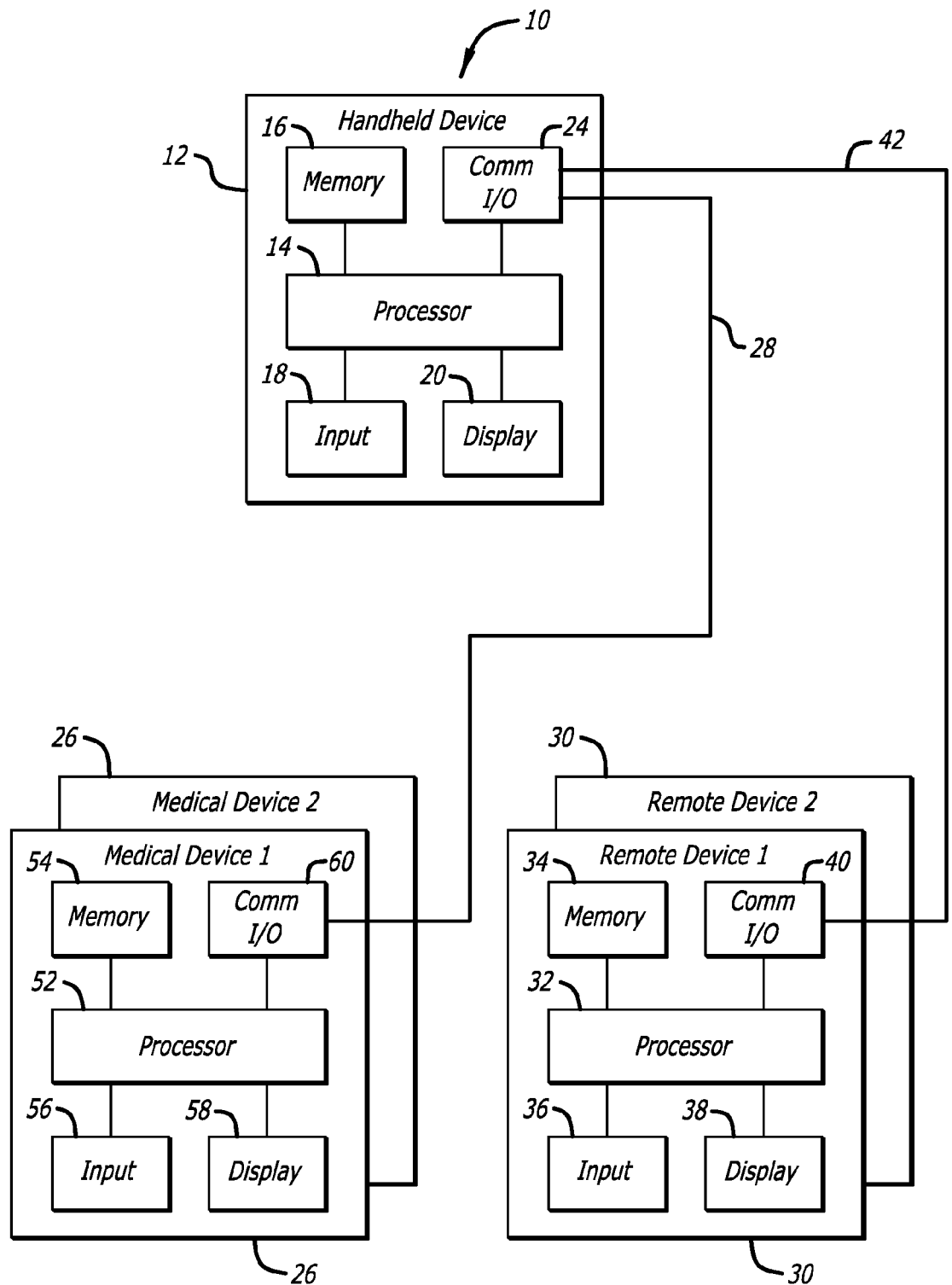
FIG. 1 is a schematic diagram illustrating an exemplary embodiment of a controller and its various components in operable communication with one or more medical devices, such as a glucose monitor or drug delivery pump, and optionally, in operable communication with a remote controller device.

Referring now to FIG. 1, a block diagram of one illustrative embodiment of a system 10 for determining drug administration information is shown. In the illustrated embodiment, the system 10 includes an electronic device 12, which may be handheld, having a processor 14 in data communication with a memory unit 16, an input device 18, a display 20, and a communication input/output unit 24. The electronic device 12 may be provided in the form of a general purpose computer, central server, personal computer (PC), lap top or notebook computer, personal data assistant (PDA), programmable telephone or cellular phone or other hand-held device, external infusion pump, glucose level meter, analyte sensing system, or the like. The electronic device 12 may be configured to operate in accordance with one or more conventional operating systems including for example, but not limited to, the Windows® operating system (distributed by Microsoft Corporation), the Linux operating system, the Mac OS® (distributed by Apple, Inc.) and embedded operating systems such as the QNX® operating system (distributed by QNX Software Systems), the eCOS® operating system (distributed by eCosCentric Limited), Windows CEO (distributed by Microsoft Corporation) and the Palm® operating system (distributed by Palm Inc.), and may be configured to process data according to one or more conventional internet protocols for example, but not limited to, NetBios, TCP/IP and AppleTalk® (Apple, Inc.). In any case, the electronic device 12 forms part of a fully closed-loop, semi closed-loop, or open loop diabetes control system.

The processor 14 is microprocessor-based, although processor 14 may alternatively be formed of one or more general purpose and/or application specific circuits and operable as described hereinafter. The processor 14 is programmed using appropriate software commands that may be stored in the memory or communicated to the processor 14 as needed. The memory unit 16 includes sufficient capacity to store data, one or more software algorithms executable by the processor 14 and other data. The memory unit 16 may include one or more conventional memory or other data storage devices. Electronic device 12 may also include an integrated glucose level meter for use in calibrating a continuous glucose monitor (CGM) or for calculating insulin amounts for bolus delivery.

The input device 18 may be used in a conventional manner to input and/or modify data. The display 20 is also included for viewing information relating to operation of the device 12 and/or system 10. Such a display may be a conventional display device including for example, but not limited to, a light emitting diode (LED) display, a liquid crystal display (LCD), a cathode ray tube (CRT) display, or the like. Alternatively or additionally, the display 20 may be or include an audible display configured to communicate information to a user, another person, or another electronic system having audio recognition capabilities via one or more coded patterns, vibrations, synthesized voice responses, or the like. Alternatively or additionally, the display 20 may be or include one or more tactile indicators configured to display or annunciate tactile information that may be discerned by the user or another person.

The input device 18 may be or include a conventional keyboard or keypad for entering alphanumeric data into the processor 14. Such a keyboard or keypad may include one or more keys or buttons configured with one or more tactile indicators to allow users with poor eyesight to find and select an appropriate one or more of the keys, and/or to allow users to find and select an appropriate one or more of the keys in poor lighting conditions. Alternatively or additionally, the input device 18 may be or include a conventional mouse or other conventional point and click device for selecting information presented on the display 20. Alternatively or additionally, the input device 18 may include the display 20 configured as a graphical user interface (GUI). In this embodiment, the display 20 may include one or more selectable inputs that a user may select by touching an appropriate portion of the display 20 using an appropriate implement. Alternatively, the display 20 may be configured as a touch-screen capable of responding to user activation to, for example, enter data or select device functions.

Alternatively, the input device 18 may also include a number of switches or buttons that may be activated by a user to select corresponding operational features of the device 12 and/or system 10. Input device 18 may also be or include voice-activated circuitry responsive to voice commands to provide corresponding input data to the processor 14. In any case, the input device 18 and/or display 20 may be included with or separate from the electronic device 12.

System 10 may also include a number of medical devices which carry out various functions, for example, but not limited to, monitoring, sensing, diagnostic, communication and treatment functions. In such embodiments, any of the one or more of the medical devices may be implanted within the user's body, coupled externally to the user's body (e.g., such as an infusion pump), or separate from the user's body. Alternatively or additionally, one or more of the medical devices may be mounted to and/or form part of the electronic device 12. Typically, the medical devices are each configured to communicate wirelessly with the communication I/O unit 24 of the electronic device 12 via one of a corresponding number of wireless communication links.

The wireless communications between the various components of the system 10 may be one-way or two-way. The form of wireless communication used may include, but is not limited to, radio frequency (RF) communication, infrared (IR) communication, Wi-Fi, RFID (inductive coupling) communication, acoustic communication, capacitive signaling (through a conductive body), galvanic signaling (through a conductive body), or the like. In any such case, the electronic device 12 and each of the medical devices include conventional circuitry for conducting such wireless communications circuit. Alternatively, one or more of the medical devices may be configured to communicate with the electronic device 12 via one or more conventional serial or parallel configured hardwire connections therebetween.

Each of the one or more medical devices 26 may include one or more of a conventional processing unit 52, conventional input/output circuitry and/or devices 56, 58 communication ports 60 and one or more suitable data and/or program storage devices 58. It will be understood that not all medical devices 26 will have the same componentry, but rather will only have the components necessary to carry out the designed function of the medical device. For example, in one embodiment, a medical device 26 may be capable of integration with electronic device 12 and remote device 30. In another embodiment, medical device may also be capable of stand-alone operation, should communication with electronic device 12 or remote device 30 be interrupted. In another embodiment, medical device 26 may include processor, memory and communication capability, but does not have a display 58 or input 56. In still another embodiment, the medical device 26 may include an input 56, but lack a display 58.

In some embodiments, the system 10 may alternatively or additionally include a remote device 30. The remote device 30 may include a processor 32, which may be identical or similar to the processor 14, a memory or other data storage unit 34, an input device 36, which may be or include any one or more of the input devices described hereinabove with respect to the input device 18, a display unit 38, which may be or include any one or more of the display units described hereinabove with respect to the display unit 20, and communication I/O circuitry 40. The remote device 30 may be configured to communicate with the electronic device 12 or medical devices(s) 26 via any wired or wireless communication interface 42, which may be or include any of the communication interfaces or links described hereinabove. Although not shown, remote device 30 may also be configured to communicate directly with one or more medical devices 26, instead of communicating with the medical device 26 through electronic device 12.

The system 10 illustrated in FIG. 1 is, or forms part of, a fully closed-loop, semi closed-loop, or open loop diabetes control arrangement. In this regard, the system 10 requires user input of some amount of information from which the system 10 determines, at least in part, insulin bolus administration information. Such insulin bolus administration information may be or include, for example, insulin bolus quantity or quantities, bolus type, insulin bolus delivery time, times or intervals (e.g., single delivery, multiple discrete deliveries, continuous delivery, etc.), and the like. Examples of user supplied information may be, for example but not limited to, user glucose level concentration, interstitial glucose level information, information relating to a meal or snack that has been ingested, is being ingested, or is to be ingested sometime in the future, user exercise information, user stress information, user illness information, information relating to the user's menstrual cycle, and the like. In any case, the system 10 includes a delivery mechanism for delivering controlled amounts of a drug; such as, for example, insulin, glucagon, incretin, or the like, and/or offering an alternatively actionable therapy recommendation to the user via the display 20, such as, for example, directions or instructions related to ingesting carbohydrates, exercising, and the like.

The system 10 may be provided in any of a variety of configurations, and examples of some such configurations will now be described. It will be understood, however, that the following examples are provided merely for illustrative purposes, and should not be considered limiting in any way. Those skilled in the art may recognize other possible implementations of a fully closed-loop, semi closed-loop, or open loop diabetes control arrangement, and any such other implementations are contemplated by this disclosure.

In a first exemplary implementation of the system 10, the electronic device 12 is provided in the form of an insulin pump configured to be worn externally to the user's body and also configured to controllably deliver insulin to the user's body. In this example, the medical devices 26 may include one or more implanted sensors and/or sensor techniques for providing information relating to the physiological condition of the user. Examples of such implanted sensors may include, but should not be limited to, a glucose sensor, a body temperature sensor, a blood pressure sensor, a heart rate sensor, one or more bio-markers configured to capture one or more physiological states of the body, such as, for example, HBA1C, or the like.

In implementations that include an implanted glucose sensor, the system 10 may be a fully closed-loop system operable in a conventional manner to automatically monitor glucose level and deliver insulin, as appropriate, to maintain glucose at desired levels. The various medical devices may alternatively or additionally include one or more sensors or sensing systems that are external to the user's body and/or sensor techniques for providing information relating to the physiological condition of the user. Examples of such sensors or sensing systems may include, but should not be limited to, a glucose strip sensor/meter, a body temperature sensor, a blood pressure sensor, a heart rate sensor, one or more bio-markers configured to capture one or more physiological states of the body, such as, for example, HBA1C, or the like.

In implementations that include an external glucose sensor, the system 10 may be a closed-loop, semi closed-loop, or open loop system operable in a conventional manner to deliver insulin, as appropriate, based on glucose information provided thereto by the user. Information provided by any such sensors and/or sensor techniques may be communicated to the system 10 using any one or more conventional wired or wireless communication techniques. In this exemplary implementation, the remote device 30 may also be included in the form of a handheld or otherwise portable electronic device configured to communicate information to and/or from the electronic device 12.

In a second exemplary implementation of the system 10, the electronic device 12 is provided in the form of a handheld remote device, such as a PDA, programmable cellular phone, or other handheld device. In this example, the medical devices 26 include at least one conventional implantable or externally worn drug pump. In one embodiment of this example, an insulin pump is configured to controllably deliver insulin to the user's body. In this embodiment, the insulin pump is configured to wirelessly transmit information relating to insulin delivery to the handheld device 12. The handheld device 12 is configured to monitor insulin delivery by the pump, and may further be configured to determine and recommend insulin bolus amounts, carbohydrate intake, exercise, and the like. The system 10 may or may not be configured in this embodiment to provide for transmission of wireless information from the handheld device 12 to the insulin pump.

In an alternate embodiment of this example, the handheld device 12 is configured to control insulin delivery to the user by determining insulin delivery commands and transmitting such commands to the insulin pump. The insulin pump, in turn, is configured to receive the insulin delivery commands from the handheld device 12, and to deliver insulin to the user according to the commands. The insulin pump, in this embodiment, may or may not further process the insulin pump commands provided by the handheld unit 12. In any case, the system 10 will typically be configured in this embodiment to provide for transmission of wireless information from the insulin pump back to the handheld device 12 to thereby allow for monitoring of pump operation. In either embodiment of this example, the system 10 may further include one or more implanted and/or external sensors of the type described in the previous example. In this exemplary implementation, a remote device 30 may also be included in the form of, for example, a PC, PDA, programmable cellular phone, laptop or notebook computer configured to communicate information to and/or from the electronic device 12.

Those skilled in the art will recognize other possible implementations of a fully closed-loop, semi closed-loop, or open loop diabetes control arrangement using at least some of the components of the system 10 illustrated in FIG. 1. For example, the electronic device 12 in one or more of the above examples may be provided in the form of a PDA, programmable cellular phone, laptop, notebook or personal computer configured to communicate with one or more of the medical devices 26, at least one of which is an insulin delivery system, to monitor and/or control the delivery of insulin to the user. As another example, the remote device 30 may be configured to communicate with the electronic device 12 and/or one or more of the medical devices 26, to control and/or monitor insulin delivery to the patient, and/or to transfer one or more software programs and/or data to the electronic device 12. The remote device 30 may reside in a caregiver's office or other remote location, and communication between the remote device and any component of the system 10 may be accomplished via an intranet, internet (such as, for example, through the world-wide-web), cellular, telephone modem, RF, or other communication link. Any one or more conventional internet protocols may be used in such communications. Alternatively or additionally, any conventional mobile content delivery system; such as, for example, Wi-Fi, WiMAX, short message system (SMS), or other conventional message scheme may be used to provide for communication between devices comprising the system 10.

Generally, the concentration of glucose in a person changes as a result of one or more external influences such as meals and exercise, and also changes resulting from various physiological mechanisms such as stress, illness, menstrual cycle and the like. In a person with diabetes, such changes can necessitate monitoring the person's glucose level and administering insulin or other glucose level altering drug, such as, for example, a glucose lowering or raising drug, as needed to maintain the person's glucose level within a desired range. In any of the above examples, the system 10 is thus configured to determine, based on some amount of patient-specific information, an appropriate amount, type and/or timing of insulin or other glucose level altering drug to administer in order to maintain normal glucose levels without causing hypoglycemia or hyperglycemia. In some embodiments, the system 10 is configured to control one or more external insulin pumps, such as, for example, subcutaneous, transcutaneous or transdermal pumps, and/or implanted insulin pumps to automatically infuse or otherwise supply the appropriate amount and type of insulin to the user's body in the form of one or more insulin boluses.

In other embodiments, the system 10 is configured to display or otherwise notify the user of the appropriate amount, type, and/or timing of insulin in the form of an insulin delivery or administration recommendation or instruction. In such embodiments, the hardware and/or software forming system 10 allows the user to accept the recommended insulin amount, type, and/or timing, or to reject it. If the recommendation is accepted by the user, the system 10, in one embodiment, automatically infuses or otherwise provides the appropriate amount and type of insulin to the user's body in the form of one or more insulin boluses. If, on the other hand, the user rejects the insulin recommendation, the hardware and/or software forming system 10 allows the user to override the system 10 and manually enter values for insulin bolus quantity, type, and/or timing in the system. The system 10 is thus configured by the user to automatically infuse or otherwise provide the user specified amount, type, and/or timing of insulin to the user's body in the form of one or more insulin boluses.

Alternatively, the appropriate amount and type of insulin corresponding to the insulin recommendation displayed by the system 10 may be manually injected into, or otherwise administered to, the user's body. It will be understood, however, that the system 10 may alternatively or additionally be configured in like manner to determine, recommend, and/or deliver other types of medication to a patient.

The system 10 is operable, as just described, to determine and either recommend or administer an appropriate amount of insulin or other glucose level lowering drug to the patient in the form of one or more insulin boluses. In order to determine appropriate amounts of insulin to be delivered or administered to the user to bring the user's glucose level within an acceptable range, the system 10 requires at least some information relating to one or more external influences and/or various physiological mechanisms associated with the user. For example, if the user is about to ingest, is ingesting, or has recently ingested, a meal or snack, the system 10 generally requires some information relating to the meal or snack to determine an appropriate amount, type and/or timing of one or more meal compensation boluses of insulin. When a person ingests food in the form of a meal or snack, the person's body reacts by absorbing glucose from the meal or snack over time. For purposes of this document, any ingesting of food may be referred to hereinafter as a "meal," and the term "meal" therefore encompasses traditional meals, such as, for example, breakfast, lunch and dinner, as well as intermediate snacks, drinks, and the like.

Figure 2:
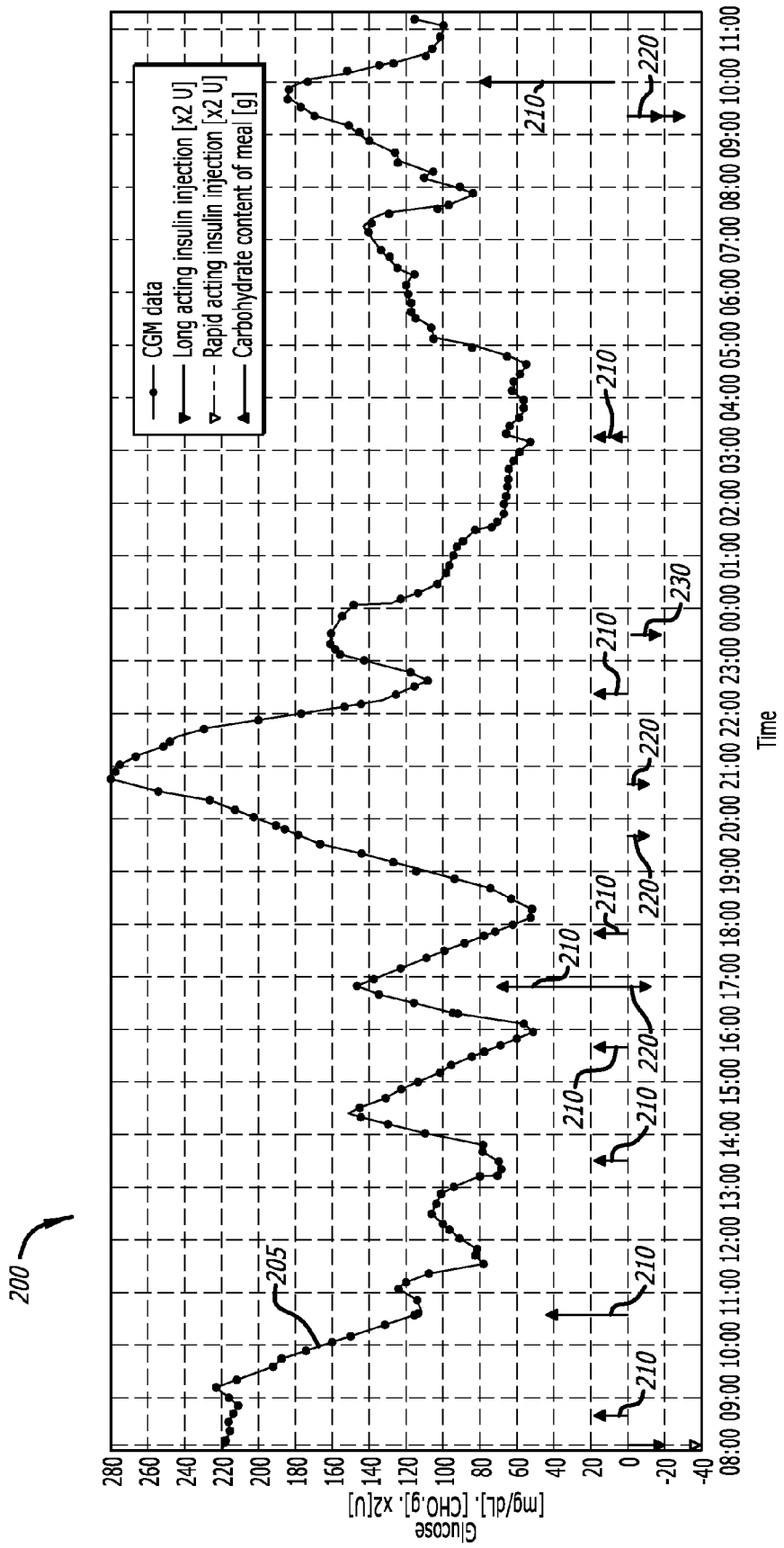
FIG. 2 is a graphical representation of a glucose profile showing glucose level measured using a CGM sensor as a function of time, and also showing the variation of the glucose level as function of carbohydrate intake and insulin administration.

FIG. 2 depicts a typical glucose absorption profile 200 for a user measured using a CGM sensor. The graph 205 plots the measured glucose level as a function of time. This profile shows the effect on glucose level of various actions, such as carbohydrate intake 210, and the delivery of rapid acting insulin 210 and long acting insulin 230.

The general shape of a glucose absorption profile for any person rises following ingestion of the meal, peaks at some measurable time following the meal, and then decreases thereafter. The speed, that is, the rate from beginning to completion, of any one glucose absorption profile typically varies for a person by meal composition, meal type or time (such as, for example, breakfast, lunch, dinner, or snack) and/or according to one or more other factors, and may also vary from day-to-day under otherwise identical meal circumstances. Generally, the information relating to such meal intake information supplied by the user to the system 10 should contain, either explicitly or implicitly, an estimate of the carbohydrate content of the meal or snack, corresponding to the amount of carbohydrates that the user is about to ingest, is ingesting, or has recently ingested, as well as an estimate of the speed of overall glucose absorption from the meal by the user.

The estimate of the amount of carbohydrates that the patient is about to ingest, is ingesting, or has recently ingested, may be provided by the user in any of various forms. Examples include, but are not limited to, a direct estimate of carbohydrate weight (such as, for example, in units of grams or other convenient weight measure), an amount of carbohydrates relative to a reference amount (such as, for example, dimensionless), an estimate of meal or snack size (such as, for example, dimensionless), and an estimate of meal or snack size relative to a reference meal or snack size (such as, for example, dimensionless). Other forms of providing for user input of carbohydrate content of a meal or snack will occur to those skilled in the art, and any such other forms are contemplated by this disclosure.

The estimate of the speed of overall glucose absorption from the meal by the user may likewise be provided by the user in any of various forms. For example, for a specified value of the expected speed of overall glucose absorption, the glucose absorption profile captures the speed of absorption of the meal taken by the user. As another example, the speed of overall glucose absorption from the meal by the user also includes time duration between ingesting of the meal by a user and the peak glucose absorption of the meal by that user, which captures the duration of the meal taken by the user. The speed of overall glucose absorption may thus be expressed in the form of meal speed or duration. Examples of the expected speed of overall glucose absorption parameter in this case may include, but are not limited to, a compound parameter corresponding to an estimate of the meal speed or duration (such as, for example, units of time), a compound parameter corresponding to meal speed or duration relative to a reference meal speed or duration (such as, for example, dimensionless), or the like.

As another example of providing the estimate of the expected speed of overall glucose absorption parameter, the shape and duration of the glucose absorption profile may be mapped to the composition of the meal. Examples of the expected speed of overall glucose absorption parameter in this case may include, but are not limited to, an estimate of fat amount, protein amount and carbohydrate amount (such as, for example, in units of grams) in conjunction with a carbohydrate content estimate in the form of meal size or relative meal size, an estimate of fat amount, protein amount and carbohydrate amount relative to reference fat, protein and carbohydrate amounts in conjunction with a carbohydrate content estimate in the form of meal size or relative meal size, and an estimate of a total glycemic index of the meal or snack (such as, for example, dimensionless), wherein the term "total glycemic index" is defined for purposes of this document as a parameter that ranks meals and snacks by the speed at which the meals or snacks cause the user's glucose level to rise. Thus, for example, a meal or snack having a low glycemic index produces a gradual rise in glucose level whereas a meal or snack having a high glycemic index produces a fast rise in glucose level. One exemplary measure of total glycemic index may be, but is not limited to, the ratio of carbohydrates absorbed from the meal and a reference value, such as, for example, derived from pure sugar or white bread, over a specified time period, such as, for example, 2 hours. Other forms of providing for user input of the expected overall speed of glucose absorption from the meal by the patient, and/or for providing for user input of the expected shape and duration of the glucose absorption profile generally will occur to those skilled in the art, and any such other forms are contemplated by this disclosure.

Generally, the concentration of glucose in a person with diabetes changes as a result of one or more external influences such as meals and/or exercise, and may also change resulting from various physiological mechanisms such as stress, menstrual cycle and/or illness. In any of the above examples, the system 10 responds to the measured glucose by determining the appropriate amount of insulin to administer in order to maintain normal glucose levels without causing hypoglycemia. In some embodiments, the system 10 is implemented as a discrete system with an appropriate sampling rate, which may be periodic, aperiodic or triggered, although other continuous systems or hybrid systems may alternatively be implemented as described above.

As one example of a conventional diabetes control system, one or more software algorithms may include a collection of rule sets which use (1) glucose information, (2) insulin delivery information, and/or (3) user inputs such as meal intake, exercise, stress, illness and/or other physiological properties to provide therapy, and the like, to manage the user's glucose level. The rule sets are generally based on observations and clinical practices as well as mathematical models derived through or based on analysis of physiological mechanisms obtained from clinical studies. In the exemplary system, models of insulin pharmacokinetics and pharmacodynamics, glucose pharmacodynamics, meal absorption and exercise responses of individual patients are used to determine the timing and the amount of insulin to be delivered. A learning module may be provided to allow adjustment of the model parameters when the patient's overall performance metric degrades such as, for example, adaptive algorithms, using Bayesian estimates, may be implemented. An analysis model may also be incorporated which oversees the learning to accept or reject learning. Adjustments are achieved utilizing heuristics, rules, formulae, minimization of cost function(s) or tables (such as, for example, gain scheduling).

Predictive models can be programmed into the processor(s) of the system using appropriate embedded or inputted software to predict the outcome of adding a controlled amount of insulin or other drug to a user in terms of the an expected glucose value. The structures and parameters of the models define the anticipated behavior.

Any of a variety of conventional controller design methodologies, such as PID systems, full state feedback systems with state estimators, output feedback systems, LQG (Linear-Quadratic-Gaussian) controllers, LQR (Linear-Quadratic-Regulator) controllers, eigenvalue/eigenstructure controller systems, and the like, could be used to design algorithms to perform physiological control. They typically function by using information derived from physiological measurements and/or user inputs to determine the appropriate control action to use. While the simpler forms of such controllers use fixed parameters (and therefore rules) for computing the magnitude of control action, the parameters in more sophisticated forms of such controllers may use one or more dynamic parameters. The one or more dynamic parameters could, for example, take the form of one or more continuously or discretely adjustable gain values. Specific rules for adjusting such gains could, for example, be defined either on an individual basis or on the basis of a user population, and in either case will typically be derived according to one or more mathematical models. Such gains are typically scheduled according to one or more rule sets designed to cover the expected operating ranges in which operation is typically nonlinear and variable, thereby reducing sources of error.

Model based control systems, such as those utilizing model predictive control algorithms, can be constructed as a black box wherein equations and parameters have no strict analogs in physiology. Rather, such models may instead be representations that are adequate for the purpose of physiological control. The parameters are typically determined from measurements of physiological parameters such as glucose level, insulin concentration, and the like, and from physiological inputs such as food intake, alcohol intake, insulin doses, and the like, and also from physiological states such as stress level, exercise intensity and duration, menstrual cycle phase, and the like. These models are used to estimate current glucose level or to predict future glucose levels. Such models may also take into account unused insulin remaining in the user after a bolus of insulin is given, for example, in anticipation of a meal. Such unused insulin will be variously described as unused, remaining, or "insulin on board."

Insulin therapy is derived by the system based on the model's ability to predict glucose levels for various inputs. Other conventional modeling techniques may be additionally or alternatively used to predict glucose levels, including for example, but not limited to, building models from first principles.

In a system as described above, the controller is typically programmed to provide a "basal rate" of insulin delivery or administration. Such a basal rate is the rate of continuous supply of insulin by an insulin delivery device such as a pump that is used to maintain a desired glucose level in the user. Periodically, due to various events that affect the metabolism of a user, such as eating a meal or engaging in exercise, a "bolus" delivery of insulin is required. A "bolus" is defined as a specific amount of insulin that is required to raise the blood concentration of insulin to an effective level to counteract the affects of the ingestion of carbohydrates during a meal and also takes into account the affects of exercise on the glucose level of the user.

As described above, an analyte monitor may be used to continuously monitor the glucose level of a user. The controller is programmed with appropriate software and uses models as described above to predict the affect of carbohydrate ingestion and exercise, among other factors, on the predicted level of glucose of the user at a selected time. Such a model must also take into account the amount of insulin remaining in the blood stream from a previous bolus or basal rate infusion of insulin when determining whether or not to provide a bolus of insulin to the user.

Continuous glucose monitoring (CGM) systems occasionally exhibit non-zero-mean signal artifacts commonly called "dropout," where the sensor signal output is momentarily lower than it should be given an interstitial glucose value. From a closed-loop control perspective, this measurement error poses an annoyance in that the falsely lower signal could trigger a momentary reduction or cessation of insulin delivery commands due to the perceived hypoglycemia event. This can result in a false alarm based either on a perceived current glucose level or a computed future glucose level.

In an embodiment of the invention, a means for reducing false hypoglycemic alarms due to a combination of a user's glucose range being mostly euglycemia (normal) and CGM system signal artifacts such as dropouts which tend to negatively bias the glucose display is presented. In such an embodiment, the threshold for detecting a hypoglycemic threshold is modified by introducing a conditional time delay such that most dropouts are shorter in duration than the time delay so that the dropouts do not trigger an alarm. Additionally, the threshold is modified appropriately so that detection of true hypoglycemic events are not delayed beyond what has been determined to be clinically safe.

It is possible, using clinical data and insulin delivery information, to tune a CGM system to provide a balance between hypoglycemic detection sensitivity and reasonable specificity that minimizes false alarms under a wide range of glucose profiles. With good glycemic control, the proportion of true-hypoglycemia may be reduced significantly enough that signal artifacts of the CGM system become an important factor in causing false alarm rates.

In one embodiment of the invention, a combination of glucose level measurements, known CGM signal artifact characteristics, and the best estimate of relevant physiological states, such as, \or example, plasma glucose, interstitial glucose, insulin onboard, and effective insulin, are used to delay the enunciation of a CGM-based hypoglycemic alarm and determine whether or not the alarm should persist. In this embodiment, instead of using an artifact detector which relies on a mechanism that is sensitive to the artifacts in the signal, the alarm instead is tuned to be insensitive to the artifacts, yet at the same time maintain a safe level of sensitivity to hypoglycemic events.

The CGM based hypoglycemic alarm of one embodiment of the invention comprises several hypoglycemic thresholds. For each threshold, there exists a timer that may potentially enunciate a hypoglycemic alarm. The lower the threshold, the shorter the amount of delay between the time the CGM measurement value is obtained and when the alarm is sounded. The amount of delay depends primarily on the level of risk associated with the delayed response to a true hypoglycemic event at a given glucose level as well as the probability of the duration of false alarms due to the presence of CGM signal artifacts at a given glucose level.

The CGM-based hypoglycemic alarm may result in the system recommending that a finger stick glucose level measurement request. If the glucose level measurement resulting from the finger stick indicates that the CGM measured hypoglycemia does not exist, the system can turn off the alarm. Alternatively, if the finger stick glucose level measurement confirms the presence of hypoglycemia, then the controller may indicate to the user that certain actions, such as taking rescue carbohydrates and/or checking glucose level frequently thereafter until the condition has been resolved, may be required.

A user with a well-controlled glucose level, using either a fully automatic closed loop system, a partial closed loop system or intensive open loop treatment, may have a glucose profile and distribution that is altered enough that the amount of false hypoglycemic alarms from the system is significantly larger than found in the general population of clinical date used to tune and confirm the hypoglycemic alarm response. The primary reason for this is that in the lower glucose range, the effect of signal artifacts from the CGM device become more dominant.

The CGM signal artifacts that reduce the effectiveness of the CGM-based hypoglycemic alarm have been found to have an a-priori distribution of severity, duration and trajectory profile. Given a user's history of glucose levels, insulin delivery, and other relevant physiological information, a particular level of hypoglycemia carries a particular level of risk in terms of the maximum delay allowed before treatment should begin to avoid the affects of severe hypoglycemia. Delaying a hypoglycemic alarm to the extent that it is still clinically safe and yet as long as possible can reduce the false alarms due to the CGM signal artifacts.

Given a glucose level confirmation and possibly a corrective action such as administering rescue carbohydrates, glucose can be estimated with sufficient confidence such that for a finite horizon in the future, there is no need to activate the CGM-based hypoglycemic alarm. This further decreases the likelihood of false alarms.

In one embodiment of the invention, the controller is programmed using appropriate software so as to set up two separate subsystems for decision making. While these subsystems will be described in terms of one or more state machines, those skilled in the art will understand that the scope of the invention is not so limited. The concept of state machines is well known to those skilled in the art of control theory and engineering. Thus, skilled artisans will understand how to program the processor to implement such a state machine.

Figure 3:
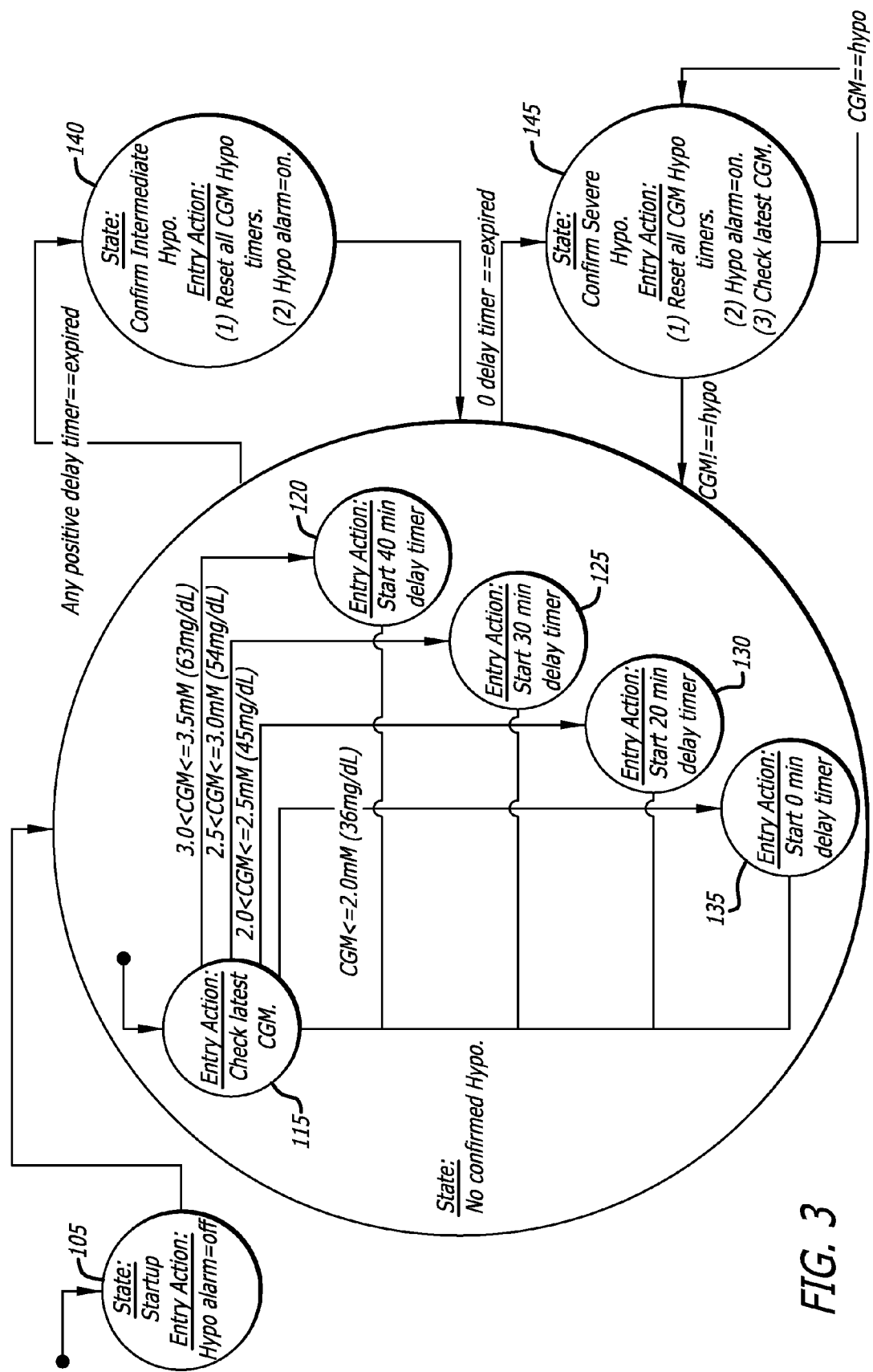
FIG. 3 is a schematic diagram of a continuous glucose monitor based subsystem, illustrated in terms of a state machine.

FIG. 3 illustrates a state machine which governs the behavior of the assertion of the CGM-based hypoglycemic detector. FIG. 3 illustrates a state machine which governs how and when confirmatory glucose level measurements, such as by a finger stick, should be taken, how and when rescue carbohydrates should be administered, and when to de-assert the CGM based hypoglycemic detector.

Referring now to FIG. 3, the purpose of the CGM state machine is to determine when a hypoglycemic alarm should be asserted relative to a CGM threshold reading. The CGM state machine begins at 105. The moment CGM measurements start to become available, the state machine enters the "no hypoglycemia confirmed" state 110. Within this state, the controller obtains a current CGM value, and, depending on the value of the measurement, controls the analysis along one of several paths. For example, if the latest CGM value (at the CGM check 115) is less than or equal to 3.5 mMol/L (63 mg/dL) but greater than 3.0 mMol/L (54 mg/dL), a delay timer of 40 minutes is implemented at state 120. If the CGM value is greater than 2.5 mMol/L (45 mg/dL) but less than or equal to 3.0 mMol/L (54 mg/dL), a delay of 30 minutes is implemented at state 125. Similarly, if the CGM value is greater than 2.0 mMol/L (36 mg/dL) but less than or equal to 2.5 mMol/L (45 mg/dL), a delay of 20 minutes is implemented at state 130.

When any of the timers set at states 120, 125 or 130 expire, and the latest CGM value is still no higher than the corresponding upper limits for the delayed timer module states 120, 125 or 130, the state changes to "confirm intermediate hypoglycemia" at state 140. In this state, the controller resets all of the timers of states 120, 125 and 130, and sets the hypoglycemia alarm to on. This state prevents the alarm from sounding unnecessarily when a user's glucose level is still within a range where the annoyance of an alarm outweighs the risk that the user is actually in a hypoglycemic condition that requires immediate attention. Once the alarm is sounded, the CGM state machine returns to the "no confirmed hypoglycemic state" 110.

Where the CGM value is less than or equal to 2.0 mMol/L (36 mg/dL), which is indicative of severe hypoglycemia, no delay is implemented, and the machine exits from the "no confirmed hypoglycemia" state 110 directly to the "confirm severe hypoglycemia" state 145. In this state, all of the timers of states 120, 125 and 130 are reset, the hypoglycemia alarm is set to on, thus sounding an alarm, and the controller continues to check the current CGM value. In this state the system cannot return to the "no confirmed hypoglycemia" state 110 until the latest CGM value rises above 3.5 mMol/L (63 mg/dL). Note that the hypoglycemia alarm, which was already activated, is related to the glucose level subsystem. The fact that the CGM subsystem state machine returns to "no confirmed hypoglycemia" 110 whether or not the latest alarm has been confirmed by a separate glucose level reading means that any time the CGM reads low values again, the potential for another false hypoglycemia alarm can be prevented.

Figure 4:
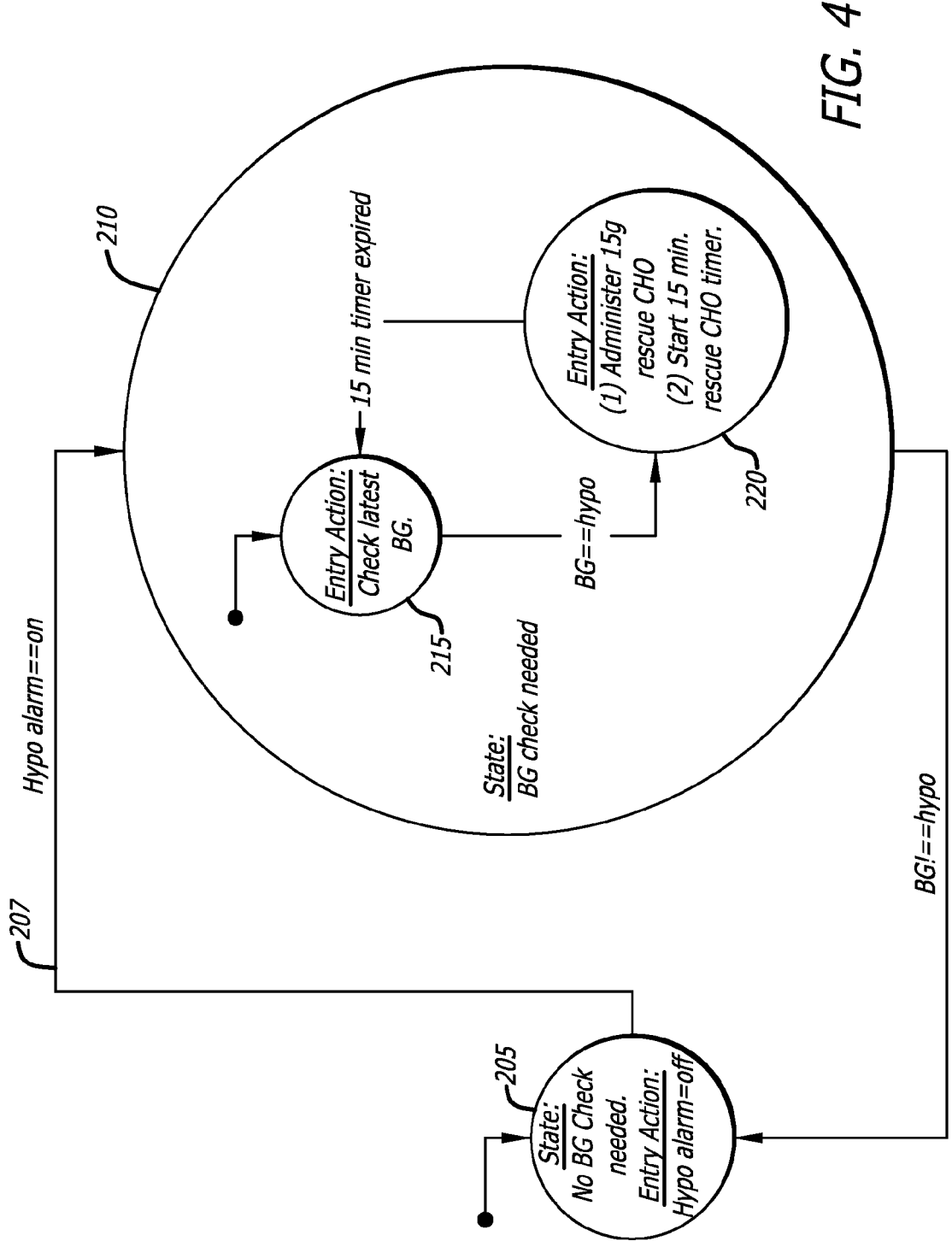
FIG. 4 is a schematic diagram of a glucose level based subsystem illustrated in terms of a state machine coupled to the continuous glucose monitor subsystem of FIG. 3.

Referring now to FIG. 4, the controller is programmed to set up a separate glucose level (BG) subsystem, which will be described in terms of a state machine. This state machine de-asserts the hypoglycemic alarm upon non-hypoglycemic confirmation using glucose level at a fixed threshold, such as when the glucose level is equal to 3.5 mMol/L (63 mg/dL). When the system starts, the BG state machine initializes into state 205. In this state, no glucose level check is needed, and the hypoglycemia alarm is set to off.

When the CGM state machine asserts the hypoglycemic alarm at states 140 or 145, the BG state machine performs a transition 207, where the BG state machine enters a "BG check needed" state 210. In this state, the system requests and waits for a finger stick glucose level measurement at 215, and, if a "BG equals hypoglycemia" confirmation results from the finger stick, the controller alerts the user at state 220. The hypoglycemia confirmation based on the BG finger stick may be set at the uppermost limit of the CGM state machine's limits, which may be equal to 3.5 mMol/L (63 mg/dL) as depicted in FIG. 2, or any other suitable value. The user may then address the low glucose level measurement by taking rescue carbohydrates at state 220. This action may be recommended by the controller. The controller also requests that another glucose level be measured in 15 minutes. This process continues until the latest glucose level indicates that the user is no longer in a hypoglycemic state.

The previous embodiments illustrated in FIGS. 3 and 4 may be generalized further by removing the actions "confirm intermediate hypoglycemia" (FIG. 3, reference number 140) and "confirm severe hypoglycemia" (FIG. 3, reference number 145) from the CGM state machine. In this embodiment, no CGM hypoglycemia timers are reset until the timers expire and the hypoglycemic alarm is enunciated. This is allows for several alarm mechanisms occurring simultaneously.

In an alternative embodiment, if the current CGM glucose value rises above 3.5 mM at any time while the CGM state machine is in the "no confirmed hypoglycemia" state 110, the alarm may be reset and the controller returns to processing incoming CGM data as before. In this case, no alarm will be sounded.

Figure 5A:
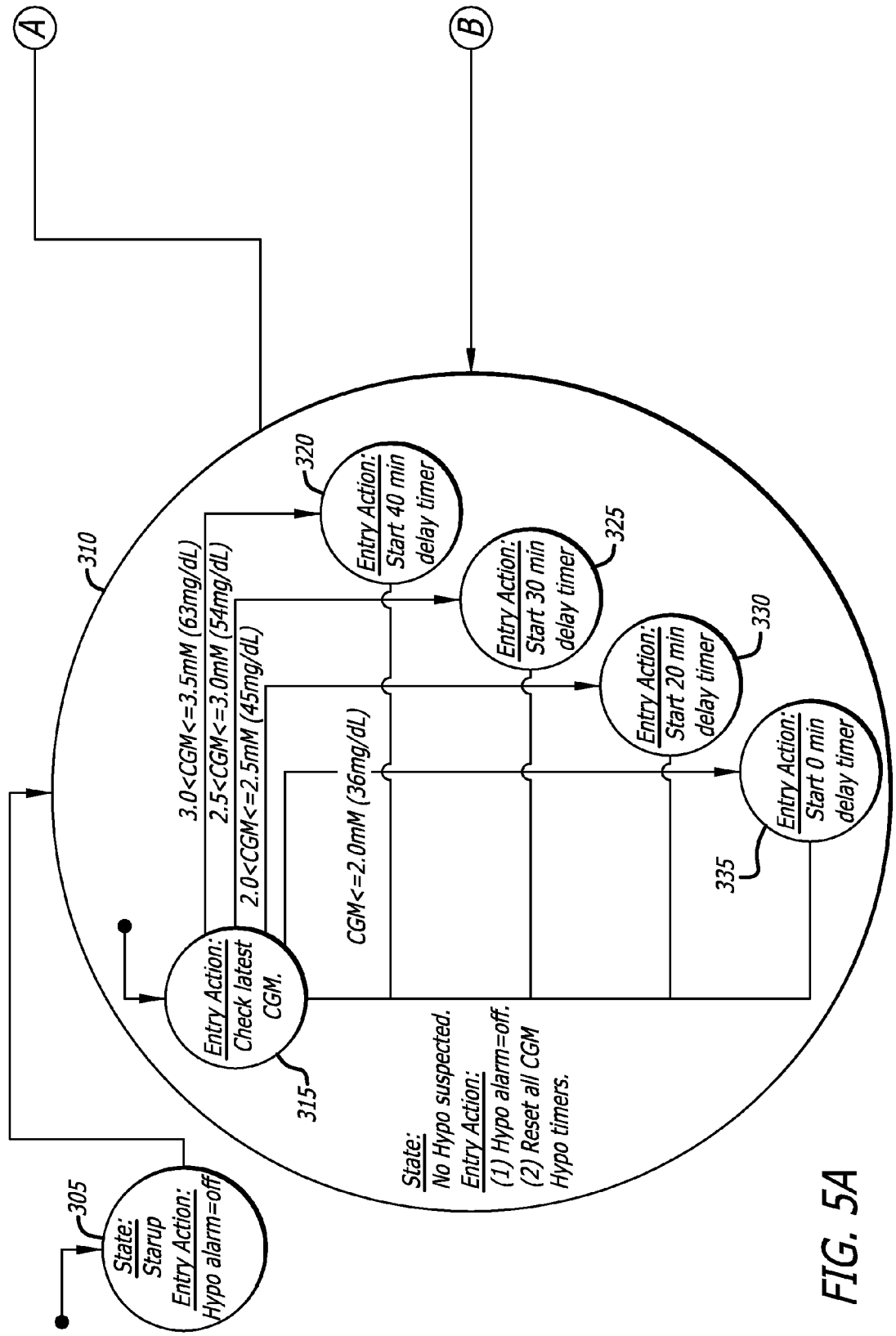
FIG. 5 is a schematic diagram of an embodiment of the invention wherein the continuous glucose monitor and glucose level state machines are coupled to a stronger degree than the embodiments shown in FIGS. 3 and 4, and also showing an additional delay timer asserted after glucose level confirmation.
Figure 5B:
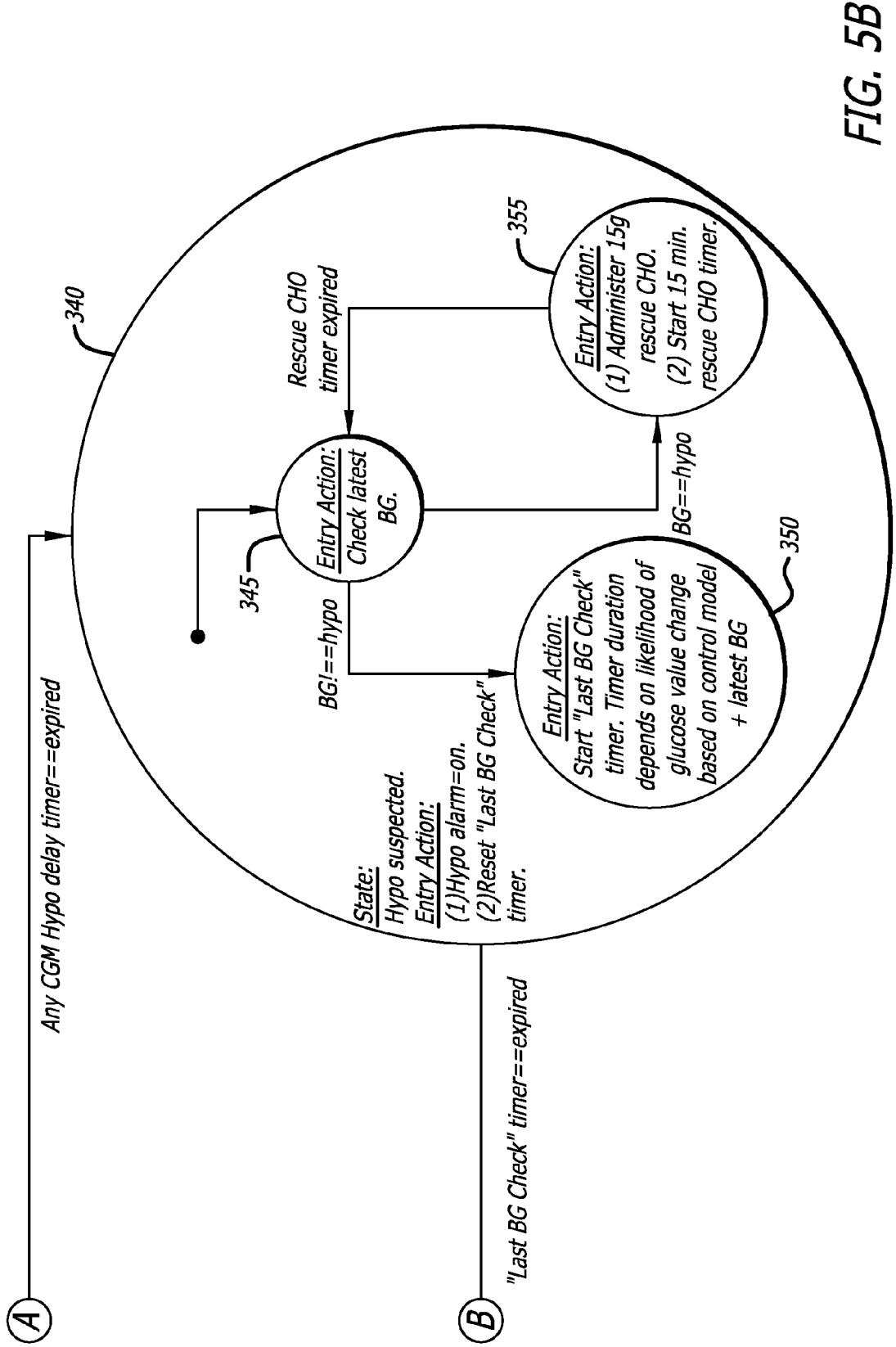

Referring now to FIG. 5, another embodiment of the invention utilizes prior knowledge of various factors such as glucose level, CGM value, insulin on board, and the like, to further minimize false alarms by adding another delayed timer. As in the embodiment of the invention depicted in FIG. 3, the CGM state machine asserts the hypoglycemic alarm, and the BG state machine de-asserts the alarm. However, the two state machines are coupled even further with the assumption that while system is at a "hypoglycemia suspected" state 340, no CGM based hypoglycemic threshold shall matter. In addition, depending on the control model and the value from the latest finger stick glucose level check, a variable time can be added to delay the return into the periodic CGM-based hypoglycemic detection "no hypoglycemia suspected" state 310.

For example, if the latest finger stick BG value is 4.0 mMol/L (72 mg/dL), and the control model predicts a rapidly rising glucose level, then a relatively long delay timer might be activated before the system transitions from "hypoglycemia suspected" state 340 to the "no hypoglycemia suspected" state 310. On the other hand, if the latest finger stick BG check indicates a glucose level value of 4.0 mMol/L (72 mg/dL) and the control model programmed into the controller predicts a rapidly dropping glucose level profile, then the system immediately transitions from the "hypoglycemia suspected" state 340 to "no hypoglycemia suspected" state 310, but the CGM based hypoglycemia detector will be given the fastest opportunity to trigger. Using the control model and relative value of the latest finger stick BG check allows the system to apply a state transition rule that is decoupled from which CGM based hypoglycemic detector triggered the state transition A simple kinetic example can be used to illustrate the processes described above. In this example, the value of time-to-return to hypoglycemia detection parameter Tr is calculated using only the latest BG value and the latest CGM rate:

$$Tr = ((BG - BG\_t)/K\_t) + (BG\_r/K\_r) \text{ if } BG > BG\_t \text{ and } BG\_r > 0,$$

$$Tr = 0 \text{ if } BG \leq BG\_t, \text{ and}$$

$$Tr = ((BG - BG\_t)/K\_t) \text{ if } BG > BG\_t \text{ and } BG\_r \leq 0;$$

where BG is the latest BG value,
BG_t is a hypoglycemic threshold,
BG_r is a model based BG rate, and
K_t and K_r are predetermined constants.

Using this approach, and assuming BG_t=4 mMol/L, K_t is 0.1 mMol/L/min, and K_r is 0.05 mMol/L/min$^2$, there are 3 distinct cases. The first case is when the latest BG while the system is in state 350 is less than or equal to BG_t (4 mMol/L). The delay is determined as Tr=0, which means that the system immediately transitions back to the "no hypoglycemia suspected" state 310, where hypoglycemic checking using CGM is active again.

The second case occurs when the latest BG while the system is in the "hypoglycemia suspected" state 350 is more than BG_t, and the estimated BG rate BG_r is negative. For this example, assume that BG=4.2 mMol/L. Then, Tr=(4.2−4.0)/0.1=2 minutes, which means that the system will transition back to the "no hypoglycemia suspected" state 310 two minutes after this latest BG measurement.

The third case occurs when the latest BG while the system is in the "hypoglycemia suspected" state 350 is more than BG_t, and BG_r is positive. For this case, assume that BG=4.2 mMol/L, and BG_r=0.5 mMol/L/min. Under this assumption, Tr=12 minutes, and the system will wait 12 minutes since the latest BG measurement before allowing hypoglycemic checking using the CGM sensor to resume. The above example uses BG measurement, a simple kinetic assumption, and a model that attempts to track the rate of the glucose level BG_r using any available information such as CGM measurements, past BG measurements, meal, and insulin history. The formation of the necessary state observer to estimate BG_r will be immediately understood by those skilled in the art.

Returning to FIG. 5, when the "hypoglycemia suspected" state 340 is entered, a finger stick BG value is requested at state 345. Depending on the glucose level profile of the user, that is, the profile due to prior insulin deliveries, insulin sensitivity, exercise and the like, the controller may enter either state 355, where rescue carbohydrates are administered and the finger stick BG is again measured after fifteen minutes, or state 350, where a timer indicating when the next finger stick BG confirmation is to be performed is started. The duration of this timer is dependent upon a determination of the likelihood of glucose value changes based on the future glucose level profile determined by the control model being used by the controller and the latest finger stick glucose level value.

In yet another embodiment, the processor is programmed using appropriate software or hardware commands to implement the following exemplary pseudo code, where glucose related parameters are specified in units of mg/dL, and time related parameters are specified in units of minutes:

```
Th = 60 mg/dL % equiv of hypo alarm threshold
Ta = time until alarm will sound
% repeat every minute...
if Glu >= Th, then Ta = 60 min
Tnew = (Glu-40 mg/dL) * 3 min/(mg/dL)
If Tnew < Ta, then Ta = Tnew
If Ta <= 0 min, the soundalarm( )
end
```

In this embodiment, the system checks the CGM value at every sample time, instead of using four or more distinct hypoglycemia thresholds with specific time delay amounts, and continues to count-down the timer until is it is larger than a latest-glucose-dependent timer.

In still another embodiment, a table of delay values as a function of glucose level is used by the processor to modify the timer delay, where crossing a lower glucose value (Glu) results in a shorter time duration (Ta). An alarm will be enunciated whenever any timer expires. An example of such a table is set forth below:

| Glu (mg/dl) | Ta (minute) |
|---|---|
| 60 | 60 |
| 55 | 45 |
| 50 | 30 |
| 45 | 15 |
| 40 | 0 |

For example, when the user's glucose level is above 60 mg/dL, the alarm will not annunciate for 60 minutes. When the user's glucose level falls below 60 mg/dL, but is above 55 mg/dL, the alarm will be delayed only 45 minutes. If the user's glucose level falls below 40 mg/dL, then the alarm annunciates immediately.

The embodiments described above are particularly useful in reducing or eliminating unacceptably large number of false hypoglycemic alarms that can desensitize a user from responding to true alarms. Such desensitization may result in harm to a user because required actions to alleviate a hypoglycemic condition would not be taken in a timely manner.

While several specific embodiments of the invention have been illustrated an described, it will be apparent that various modifications can be made without departing from the spirit and scope of the invention. Accordingly, it is not intended that the invention be limited, except as by the appended claims.

We claim:
1. An electronic analyte monitoring system comprising:
an electronic analyte monitor comprising an implantable analyte sensor;

a processor configured to receive a signal from the electronic analyte monitor indicative of an analyte level obtained from the implantable analyte sensor, wherein the signal can indicate the analyte level as falsely low, the processor also adapted to recursively analyze the signal in accordance with one or more software commands, the one or more software commands programming at least a portion of the processor to operate as a state machine with states comprising:

a no hypoglycemia confirm state during which the analyte level is compared to a first threshold, the no hypoglycemia confirm state having a predetermined time delay for activation of an alarm where a duration of the predetermined time delay is dependent on a value of the analyte level, wherein the predetermined time delay is initiated if the analyte level is below the first threshold and, after being initiated, the predetermined time delay is reset if the analyte level rises above the first threshold and the predetermined time delay has not yet expired; and a confirm hypoglycemia state that is entered if the analyte level is below the first threshold after expiration of the predetermined time delay, the confirm hypoglycemia state causing generation of the alarm; and wherein the processor is further coupled to a memory on which instructions are stored, wherein the instructions, when executed by the processor, cause the processor to transmit a command to cause adjustment of a medication delivery rate when there is a confirm hypoglycemia state.

2. The system of claim 1, wherein the duration of the predetermined time delay is a first length when the analyte level is below the first threshold and above a second threshold.

3. The system of claim 2, wherein the duration of the predetermined time delay is a second length when the analyte level is below the second threshold, the second length being less than the first length.

4. The system of claim 3, wherein the state machine further comprises:

a confirm severe hypoglycemia state that is entered when the analyte level is below a third threshold that is less than the second threshold and indicative of severe hypoglycemia, the confirm severe hypoglycemia state causing generation of the alarm.

5. The system of claim 2, wherein the predetermined time delay is a first predetermined time delay and, if the duration of the first predetermined time delay is set to the first length and the analyte level falls below the second threshold, the no hypoglycemia confirm state initiates a second predetermined time delay having a second length that is less than the first length, and wherein the confirm hypoglycemia state is also entered if the analyte level is below the second threshold after expiration of the second predetermined time delay, the confirm hypoglycemia state causing generation of the alarm.

6. The system of claim 5, wherein if the confirm hypoglycemia state is entered thereby causing generation of the alarm, all predetermined time delays that have not yet expired are reset.

7. The system of claim 1, wherein generation of the alarm occurs with display of a first message to the user to perform a blood glucose measurement.

8. The system of claim 7, wherein the state machine further comprises:

a blood analyte level check state that receives a blood analyte level measurement and determines whether a hypoglycemic condition is present and, if so, displays a second, corresponding message to the user.

9. The system of claim 8, wherein the second message to the user recommends administration of rescue carbohydrates.

10. A method for determining when to adjust a medication delivery rate and to present a hypoglycemic alarm to a user of an electronic analyte monitoring system comprising an electronic analyte monitor, an implanted analyte sensor of the electronic analyte monitor, and a processor device adapted to recursively analyze a signal from the electronic analyte monitor in accordance with one or more software commands, wherein the signal can indicate an analyte level that is falsely low, and wherein the one or more software commands program at least a portion of the processor device to operate as a state machine with states comprising a no hypoglycemia confirm state and a confirm hypoglycemia state, the method comprising:

sensing an analyte level with the implanted analyte sensor of the electronic analyte monitor;

receiving, by the processor device, the signal from the electronic analyte monitor, wherein the signal is indicative of the analyte level obtained from the implanted analyte sensor;

comparing, by the processor device in the no hypoglycemia confirm state, the analyte level to a first threshold, initiating, by the processor device in the no hypoglycemia confirm state, a predetermined time delay for activation of an alarm if the analyte level is below the first threshold, wherein a duration of the predetermined time delay is dependent on a value of the analyte level;

resetting, by the processor device in the no hypoglycemia confirm state, the predetermined time delay if the analyte level rises above the first threshold and the predetermined time delay has not yet expired;

causing generation of the hypoglycemic alarm, by the processor device in the confirm hypoglycemia state, if the analyte level is below the first threshold after expiration of the predetermined time delay; and transmitting a command to cause an adjustment of a medication delivery rate when there is a confirm hypoglycemia state.

11. The method of claim 10, wherein the state machine further comprises a confirm severe hypoglycemia state and the method further comprises:

causing generation of the alarm, by the processor device in the confirm severe hypoglycemia state, if the analyte level is below a second threshold that is less than the first threshold and indicative of severe hypoglycemia.

12. The method of claim 10, wherein the duration of the predetermined time delay is a first length when the analyte level is below the first threshold and above a second threshold.

13. The method of claim 12, wherein the duration of the predetermined time delay is a second length when the analyte level is below the second threshold, the second length being less than the first length.

14. The method of claim 13, wherein the state machine further comprises a confirm severe hypoglycemia state and the method further comprises:

causing generation of the alarm, by the processor device in the confirm severe hypoglycemia state, if the analyte level is below a third threshold that is less than the second threshold and indicative of severe hypoglycemia.

15. The method of claim 12, wherein the predetermined time delay is a first predetermined time delay and the method further comprises:
  initiating, by the processor device in the no hypoglycemia confirm state, a second predetermined time delay having a second length that is less than the first length, the second predetermined time delay being initiated if the duration of the first predetermined time delay is set to the first length and the analyte level falls below the second threshold; and
  causing generation of the alarm, by the processor device in the confirm hypoglycemia state, if the analyte level is below the second threshold after expiration of the second predetermined time delay.

16. The method of claim 15, comprising:
  if the alarm is caused to be generated by the processor device in the confirm hypoglycemia state, then resetting, by the processor device, all predetermined time delays that have not yet expired.

17. The method of claim 10, comprising:
  displaying a first message to the user to perform a blood glucose measurement along with the alarm.

18. The method of claim 17, wherein the state machine further comprises a blood analyte level check state, the method comprising:
  receiving, by the processor device in the blood analyte level check state, a blood analyte level measurement and determining whether a hypoglycemic condition is present; and
  displaying a second message to the user if a hypoglycemic condition is present.

19. The method of claim 18, wherein the second message to the user recommends administration of rescue carbohydrates.

* * * * *